United States Patent [19]

Morrey, Jr.

[11] Patent Number: 5,130,651
[45] Date of Patent: Jul. 14, 1992

[54] METHOD AND APPARATUS FOR PROVIDING COMPENSATION FOR VARIATIONS IN PROBE-SURFACE SEPARATION IN NON-CONTACT EDDY CURRENT INSPECTION SYSTEMS

[75] Inventor: Willard C. Morrey, Jr., Palm City, Fla.

[73] Assignee: United Technologies Corporation, Hartford, Conn.

[21] Appl. No.: 580,279

[22] Filed: Sep. 10, 1990

[51] Int. Cl.$^5$ .................. G01R 33/12; G01N 27/82
[52] U.S. Cl. .................................. 324/225; 324/202; 324/226
[58] Field of Search .............. 324/202, 225, 226, 262; 364/571.01, 571.04, 571.05, 571.07

[56] References Cited

U.S. PATENT DOCUMENTS 4,761,610  8/1988  Svegander et al. ............... 324/226

Primary Examiner—Walter E. Snow
Attorney, Agent, or Firm—McCormick, Paulding & Huber

[57] ABSTRACT

A non-contact eddy current inspection system provides for compensation for variations in the distance between the eddy current probe and the workpiece surface. Probe height from the surface is first determined for a scan using a vector analysis of the signals through inductive coils. Height compensated data signals are then compared against a threshold value to determine the presence of flaws in a workpiece surface.

10 Claims, 4 Drawing Sheets

METHOD AND APPARATUS FOR PROVIDING COMPENSATION FOR VARIATIONS IN PROBE-SURFACE SEPARATION IN NON-CONTACT EDDY CURRENT INSPECTION SYSTEMS

TECHNICAL FIELD

The present invention relates to eddy current fault detection systems and more particularly to eddy current fault detection systems characterized by compensation for varying probe-workpiece separation.

BACKGROUND OF THE INVENTION

Fault detection devices employing eddy currents generated in a workpiece surface are known in the art and include a probe with one or more inductive coils. An electromagnetic signal is provided to the coils. As the coils are moved relative to the workpiece surface, a small fault or defect (e.g. a crack) located therein will cause a change in the magnetic flux density. This change will be reflected as a perturbation in the impedance characteristics of the electrical circuit of which the coils are a part. The electrical circuit is configured so that the magnitude of a perturbation of an electrical signal therein is correlated to the magnitude of the defect.

An example of such an eddy current instrument is the Nortec NDT 25. The Nortec instrument is capable of flaw detection in a workpiece surface or it can measure the thickness of non-conductive coatings such as paints. The Nortec NDT 25 is used with a probe having one or two inductive coils with a core and is designed to operate over a range of selected signal frequencies in accordance with the desired range of defect size. An example of a known probe is the Pratt & Whitney TAM 189532.

Prior art eddy current detection devices require the inductive probe to be positioned at a fixed distance from the surface of the workpiece. Very accurate probe-workpiece spacing must be maintained since variations in probe distance from the workpiece surface will alter the output signal magnitude; rendering accurate assessment of flaw size (or even presence) impossible. Eddy current flaw detection devices have either been one of two types. Contact devices are configured with an outer surface of the probe that remains in contact with the workpiece surface throughout a scan. Other devices have the probe positioned off the workpiece surface by an intermediate element, such as an air bearing. Contact devices are undesirable since the contact surface of the probe will wear in a very short time so that the distance will vary by an indeterminate amount. In addition, the rate of wear of the probe contact surface increases with the speed at which the probe is moved across the workpiece surface. The faster the measurement, the more quickly the probe will wear. Eddy current flaw detection devices using air bearings or the like are undesirable, sure they are mechanically complicated and are liable to fail.

The workpieces themselves have varying surface contours. Initially the probe is positioned at a selected distance from a point on the workpiece surface. As it moves thereacross, the separation will vary. Often workpieces may assume a "tin can" or "potato chip" surface configuration. That is, the workpiece may bow inwardly or outwardly in a manner similar to a metal can or assume a saddle shape akin to that of a potato chip. With many devices the variation will be of a magnitude greater than the probe-workpiece spacing, resulting in contact therebetween and damage to the probe.

It would be advantageous to have an eddy current surface flaw detection method and apparatus for detecting workpiece surface flaws which would compensate for inductive probe-surface height variations. The present invention is drawn towards such a method and apparatus.

SUMMARY OF THE INVENTION

An object of the present invention is to provide a system for fault detection in a workpiece surface having a noncontact eddy current probe characterized by compensation for variations in the probe-workpiece surface separation.

Another object of the present invention is to provide for an eddy current fault detection system capable of high speed operation.

According to the present invention, a system for use in determining the presence of flaws in a workpiece having a surface, includes a probe having at least one inductive coil in a tip, with the probe tip located in noncontacting proximity to the workpiece surface. A probe movement mechanism is provided to controllably advance the probe across the surface. An eddy current signal generator is electrically coupled with the probe mechanism and a second inductive coil is provided which together comprise a null balanced circuit. In operation the circuit has an electrical signal flowing there through. A computer receives data signals from the eddy current signal generator and provides control signals to the eddy current signal generator and the probe movement mechanism to control the operation thereof in accordance with an algorithm that includes the steps of: generating control signals to advance the probe across a surface flaw of a standard magnitude; calibrating the system by generating a table of signals corresponding to the amplitude of the circuit signal as a function of probe-workpiece surface separation distance as the probe is advanced across the standard flaw; and generating baseline vector signals corresponding to the vector magnitude of the circuit signals as the probe is scanned across the workpiece surface as a function of probe-workpiece surface separation distance. The algorithm also includes the steps of scanning the workpiece surface with the probe to generate scan data signals; determining from the scan data signals values of probe-workpiece surface separation distance per unit length of the workpiece surface scan by computing vector magnitudes therefor; comparing each of the scan data signals with the standard flaw signals at the equivalent probe-workpiece surface separation distance; and providing a signal indicative of a flaw should the magnitude of a scan data signal exceed a preselected flaw threshold value.

DESCRIPTION OF THE PREFERRED EMBODIMENT

Figure 1:
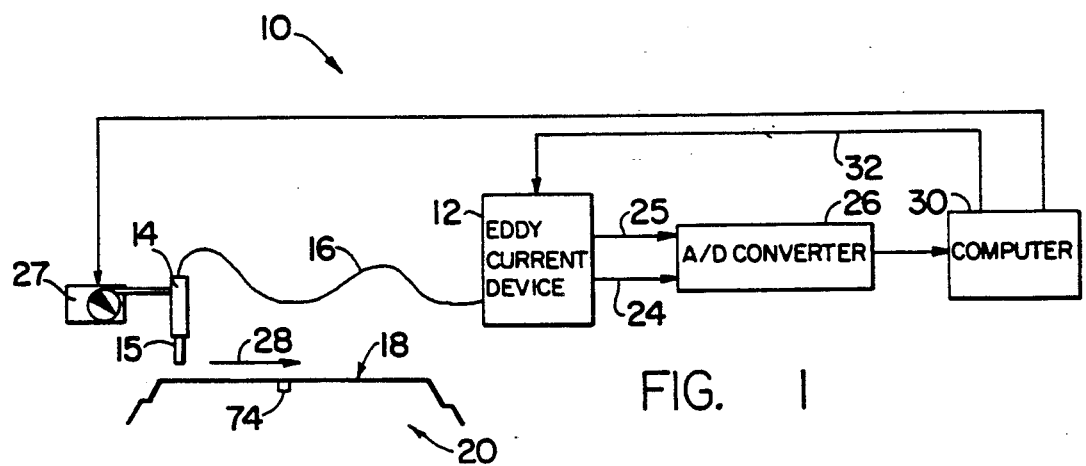
FIG. 1 is a simplified schematic illustration of a height compensated eddy current fault detection system provided according to the present invention.
Figure 2:
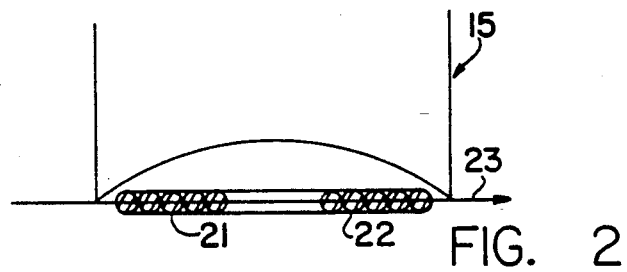
FIG. 2 is a simplified illustration of a probe tip provided by the system of FIG. 1.

Referring now to FIG. 1 there is shown a simplified schematic illustration of a height compensated eddy current fault detection system provided according to the present invention. The system 10 is comprised of a eddy current measurement instrument 12 having a probe 14 connected therewith by a lead 16. The instrument 12 is of a known type, such as a Nortec NDT 25. The probe includes one or two inductive coils depending upon whether it is of an absolute (one coil) or differential (two coil) configuration. In the system of FIG. 1, the probe comprises a Pratt & Whitney TAM 189532 1/16 inch reflective differential prove having two receive coils and drive coils in a tip 15. Those skilled in the art will note that absolute probes require a second, reference coil to be configured with the eddy current device. The preferred probe is configured to operate with a 2 MHtz signal for examing flaws in surface 18 of workpiece 20 on the order of 0.005 inch×0.010 inch in inconel or titanium jet engine parts. As shown schematically in FIG. 2, probe receive coils 21, 22 in the preferred embodiment are located adjacent one another and are arranged along an axis 23. Those skilled in the art will note that differential coils must be made with sufficient imbalance between the inductive parts thereof such that a variation of 0.001 inch is measurable above the random noise signal level.

The Nortec device includes 2 output channels schematically indicated at 21 (channel 1) and 25 (channel 2). A visual display is included. An analog to digital (A/D) converter 26 is provided for digitizing the analog output signals from the Nortec device. Some other devices directly provide digitized signals without a separate A/D converter. The probe is moved in response to control signals from the computer relative to the workpiece by an appropriate mechanism, including translation device 27, which advances the probe over the fixed workpiece along an axis 28 parallel to axis 20. These signals are provided to a computer 30 which executes algorithms to control the operation of the eddy current device and the translation device in accordance with the present invention. Those skilled in the art will note that the workpiece can be moved relative to a fixed probe. For example, planar jet engine discs are located on a turntable and rotated relative to a fixed probe during the flaw detection process. The operation of the eddy current device is also controlled by the computer by means of signals presented on lines 32.

The Nortec device is configured to provide impedance plane signal analysis. The device displays in a known manner a plot of the real and imaginary parts of the impedance of a balanced electrical circuit, such as the circuit formed by the Nortec device and probe. The probe tip is positioned in close proximity (eg, 0.003 inch) to the surface such that the magnetic induction from current flow through the coils will be affected thereby. As the probe moves across a homogeneous surface, the magnetic induction and hence circuit impedance will remain approximately constant. However, when the probe encounters a crack or other flaw in the workpiece, a change in the circuit impedance results in a change in the amplitude in the signal flowing through the circuit. A differential coil perturbed in this manner will, for each coil or channel, yield a signal having positive and negative portions as a function of time when a flaw is encountered (see FIG. 4), while an absolute probe will yield a signal spike.

In the preferred system, the output signal's dynamic range is plus or minus 10 V corresponding to a digitized output signal range of 0–4095 counts, with O V approximately equal a 2048 count baseline. The output signal of the device is two channel, one for each coil. The display can be configured to be a single channel on the vertical axis versus time on the horizontal axis. Alternatively, the display can be configured to show the channel one signal versus the channel two signal along the display axes. The computer will receive the two channel output data for similar processing. The computer is programmed to perform the computations detailed herein and generate the specified parameters in a manner adapted to the particular computer employed.

Figure 3:
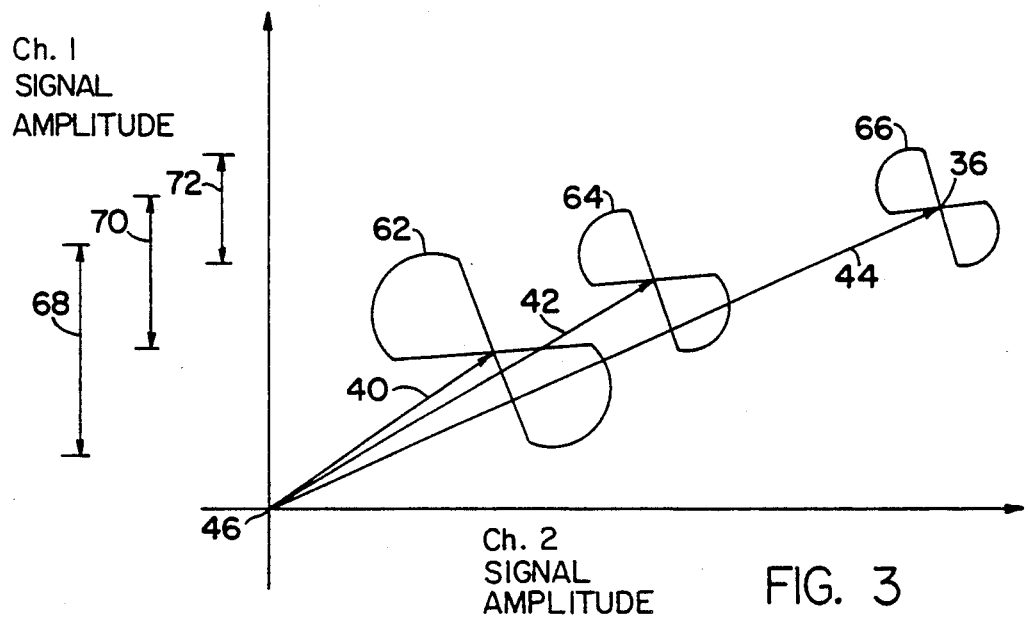
FIG. 3 is a diagrammatic illustration showing the response of the system of FIG. 1 to the detection of a surface fault in a workpiece.

The circuit is nulled in a known manner. When the probe is placed at a distance, D, from the workpiece surface, the output signal appears as a horizontal line advancing across the display. In impedance plane analysis mode, the output signals approximate a point displaced from an origin. The location of this point varies with probe-surface separation. In FIG. 3, points 32–36 of output signal display 38 are signal traces at different values of D. Points 32–36 each have a vector length 40, 42, 44 from an origin 46. These lengths are determined by the computer in a known manner.

Figure 4:
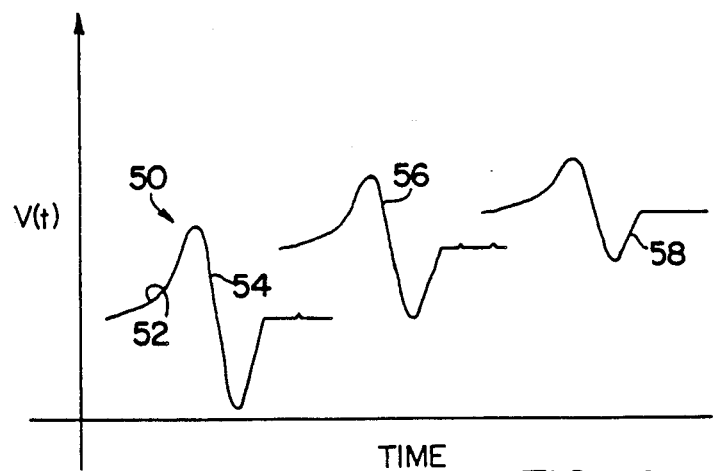
FIG. 4 is a diagrammatic illustration showing the response of the system of FIG. 1 as a function of time to the detection of a surface fault in a workpiece.

When moved along a flawless workpiece surface, the signal will remain essentially at the baseline so long as the configuration of the workpiece remains constant. Variations caused by cracks or other defects therein will cause a change in the magnetic flux through the coils and hence changes in the eddy currents flowing therein. Referring now to FIG. 4, there is shown a display 48 of the Nortec device with an output signal of a single channel (curve 50). The first portion 52 of curve 50 corresponds to the output signal as it is passed over a homogeneous workpiece surface. As the coils approach a crack or other flaw, impedance changes are generated in the coils due to the change in eddy current flow through the flaws. These impedance changes are represented by the second portion 54 of curve 50.

The magnitude of the output signals (i.e. the amplitude of curve 50 in FIG. 4) are related to the size of the defect. In addition, the amplitude of the output signals are related to the distance of the probe from the workpiece surface. Since both of these parameters are of the same magnitude, it is imperative that the distance from the workpiece surface be accurately assessed to insure that the magnitude of the surface flaws are properly represented. For example, in FIG. 4 curves 56 and 58 correspond to the channel 1 output signal as the same flaw is scanned but at increased probe-surface distances. Note that the amplitude of the signal is decreased and the position of the curve is moved relative to the origin 60. Similarly in FIG. 3, the same three scans generate curves 62, 64 and 66. Note that the respective channel 1 signal amplitudes are indicated by arrows 68, 70 and 72.

The prior art assumed it was essential to have the workpiece-probe separation held constant. This was done in a number of ways, including having a contact probe wherein the coil to workpiece surface distance is fixed by a separating element or another device which held the probe off the surface of the workpiece, such as an air bearing. In contrast, the present invention eschews attempts to maintain the workpiece-probe separation; attempts which succeed only in limiting measurement speed or in complicating the apparatus and increasing its cost.

The present invention compensates for varying separation between the eddy current probe and the workpiece surface. To do so it is necessary to calibrate the output signals from the eddy current instrument. In that process the response of the system to the presence of a known flaw must be determined. A standard flaw signal generator (74, FIG. 1) comprises a small precision machined slot in a conductive material surface similar to the material which is to be examined or a small standardized wire embedded in a nonconductive material. The signal generator is scanned by the probe at a specified distance therefrom. In the preferred embodiment the distance selected to be approximately 0.003 inch. The minimum peak to peak signal at this distance is approximately 800 counts, with the preferred A/D converter having a dynamic range of 20 volts (±10 volt) corresponding to a digital signal range of between 0 and 4095 counts.

Those skilled in the art will note that the amplitude of the signal must be set initially high enough to be measurable when the distance between the probe and the workpiece surface is increased to the maximum separation expected during inspection. Since the correct value of a data point cannot be determined if the eddy current measurement instrument digitized signal reads either 0 or 4095 counts (A/D converter saturated), a scan has to be redone either close to the surface or further away therefrom in order to obtain valid data. To minimize occurrences such as these, it is advantageous to determine a height above the workpiece surface at which the probe can be known and still obtain data in an unsaturated state at 0.001 inch from the surface. This optimum distance is determined preferably by nulling the system at 0.001 inch from the surface, and moving away until the signal is within a preselected safety factor of saturation. A nulled system at this height will leave a safety factor of 0.001 inch in the opposite direction.

Figure 5:
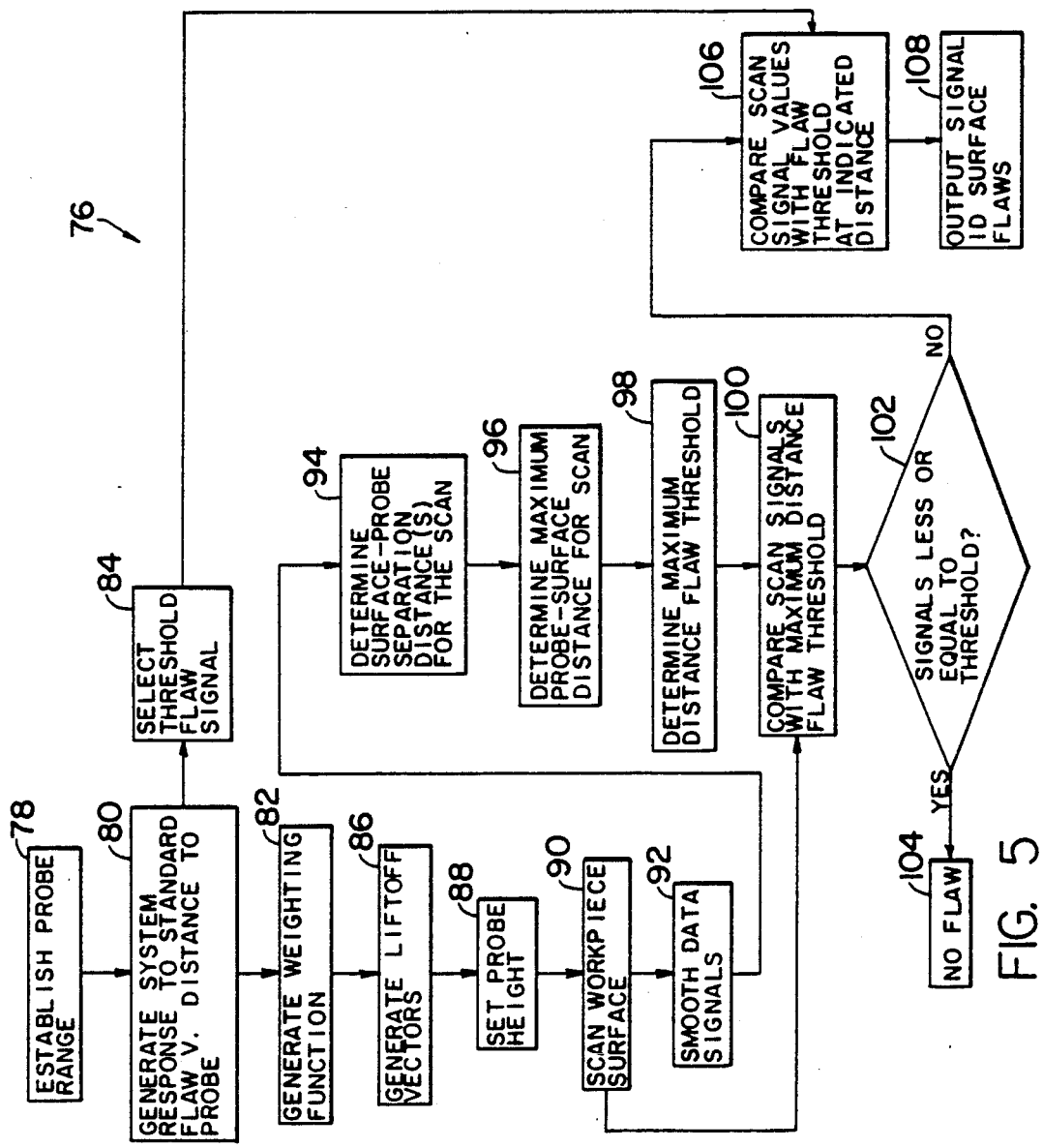
FIG. 5 is a diagrammatic illustration of a first algorithm executed by the system of FIG. 1

An algorithm 76 executed by the system 10 is schematically shown in FIG. 5. Initially at block 78 the scan minimum surface to probe distance must be determined, as care must be taken to avoid the undulating surface moving to contact the probe during measurement. This may be done in any number of known methods, including step profiling. A series of "touch" measurements may also be taken with a contact probe in a known manner to establish the minimum distance between the probe and surface to ensure the probe 14 does not contact the surface during measurement. As noted above, the response of the system to a standard flaw or signal generator must be determined over the probe measurement range (block 80).

The probe is repeatedly advanced across the standard flaw in a series of scans with the distance between the probe and the surface containing the signal generator being varied with each scan, generating a table of amplitude vs. probe-surface distances. Exemplary values are found in table 1, where "D" corresponds to the probe surface distance and "AMP" corresponds to the signal amplitude count determined for the signal generator.

TABLE 1

| D | Amp (counts) |
|---|---|
| 0.002 | 860 |
| 0.003 | 800 |
| 0.004 | 750 |
| 0.005 | 710 |
| \| | \| |
| 0.010 | 550 |
| \| | \| |
| 0.015 | 350 |
| \| | \| |
| 0.020 | 200 |

Intermediate points are established by direct measurement or by interpolation, depending upon the application. Using this data a weighting function is calculated by the computer at block 82 which corresponds to a table of factors necessary to normalize the output signal to that taken at the standard distance, $D_0$ (0.003 inch in the preferred embodiment). Table 2 corresponds to the table of factors generated from the data of table 1.

TABLE 2

| D | F/D Factor |
|---|---|
| 0.002 | 0.9302 |
| 0.003 | 1.0000 |
| 0.004 | 1.0667 |
| 0.005 | 1.1268 |

At block 84 a threshold value of flaw size is selected in dependence on the particular object being scanned. The probe is moved to the workpiece and nulled at the optimum distance as described above. The baseline signal corresponds to the absence of a flaw and has a magnitude of 2048 counts in each channel or approximately half of the dynamic range of the device. A series of "liftoff" baseline signal measurements are taken (block 86). These are measurements of the position of the output signal from an origin. As noted above in the display the origin is at the lower left. A table of values ($V_D$) corresponding to distances from the surface is computed by measuring a baseline vector with the probe at several distances from the workpiece surface.

TABLE 3

| D | V/D Vector | Chan 1 | Chan 2 |
|---|---|---|---|
| 0.002 | 2687 | 1900 | 1900 |
| 0.003 | 2896 | 2048 | 2048 |
| 0.004 | 3288 | 2350 | 2300 |
| 0.005 | 3514 | 2470 | 2500 |
| \| | \| | \| | \| |
| 0.010 | 3903 | 2750 | 2770 |
| \| | \| | \| | \| |
| 0.015 | 4108 | 2900 | 2910 |
| \| | \| | \| | \| |
| 0.020 | 4250 | 3010 | 3000 |

In Table 3, "D" corresponds to the separation of the workpiece and the probe. "Chan 1" and "Chan 2" correspond to the signal counts in each of the respective channels for that distance. The corresponding "Vector" values are the vector length as measured from the origin.

Those skilled in the art will note that with known flaw detection techniques a lift-off (phase angle) correction is made by adjusting the phase angle of the Nortec device to move the lift-off signal into a horizontal position that is, such that the probe when moved slightly from the distance $D_0$ will traverse a horizontal line on the display (i.e., no change in channel 1 value with probe-surface separation). In contrast, baseline signal vector values are generated in the present invention. The baseline signal vector is measured similar to those intervals used to generate the values of Table 1. Here again, intermediate points may either be measured directly or interpolated. The vector must maintain an approximate monotonic increase (i.e. not decrease in value) so as to generate a unique vector magnitude for each probe distance. If the measured vector is not determined to be monotonic, the phase angle between the signal channels is adjusted in an attempt at correction. Should a monotonic increase not be obtainable, a different probe should be employed.

At block 88 the probe is set above the workpiece surface at the distance sufficient to avoid the probe contact during the scan. The workpiece is then scanned, with typically 250 pairs of data points taken per inch of scan (block 90). The data signals pairs correspond to the magnitude of the signal levels in each coil as the probe is moved across the surface. In the system 10, the data is provided from the Nortec device to the computer via the A/D converter where it is stored for further processing. At block 92 the data for each channel is smoothed using known techniques to eliminate the possibility that signals associated with a flaw would adversely effect the probe to surface distance determination. A 20 point running average is preferably used.

The probe-surface distance is determined for intervals of the scan of a preselected length. Typically a distance is calculated for each inch of scan (block 94). Vector lengths as defined above are computed for each inch by comparing the magnitude of the computed vector with the vector magnitude function previously determined. Table 4 contains probe surface distances for each inch in a 7 inch scan.

TABLE 4

| Inch # | Vector | Chan 1 | Chan 2 | D |
|---|---|---|---|---|
| 1 | 3400 | 2404 | 2404 | 0.00449 |
| 2 | 3350 | 2369 | 2369 | 0.00427 |
| 3 | 3288 | 2350 | 2300 | 0.004 |
| 4 | 3150 | 2227 | 2227 | 0.00327 |
| 5 | 3000 | 2121 | 2121 | 0.00263 |
| 6 | 2900 | 2050 | 2051 | 0.00226 |
| 7 | 2950 | 2086 | 2086 | 0.00245 |

At block 96 the maximum probe-surface distance is determined for that scan. The maximum distance flaw threshold is determined by reference to the value set forth previously in table 1 (block 98). The non-smoothed channel 1 scan signals are searched for peak to peak amplitudes which are compared with the maximum distance of flaw threshold value at block 100. If the scan amplitude is less than or equal to the maximum distance flaw threshold value (block 102), then no flaw is possible at that point of the scan and that data point is eliminated from further analysis (block 104).

However, should the scan value exceed the maximum distance flaw threshold value the algorithm next will compare the scan signal values with the flaw threshold values at the indicated distance (block 106). An output signal indicative of a surface flaw is provided should the comparison result in a peak to peak signal value in excess of the flaw threshold at that distance (block 108).

Figure 6:
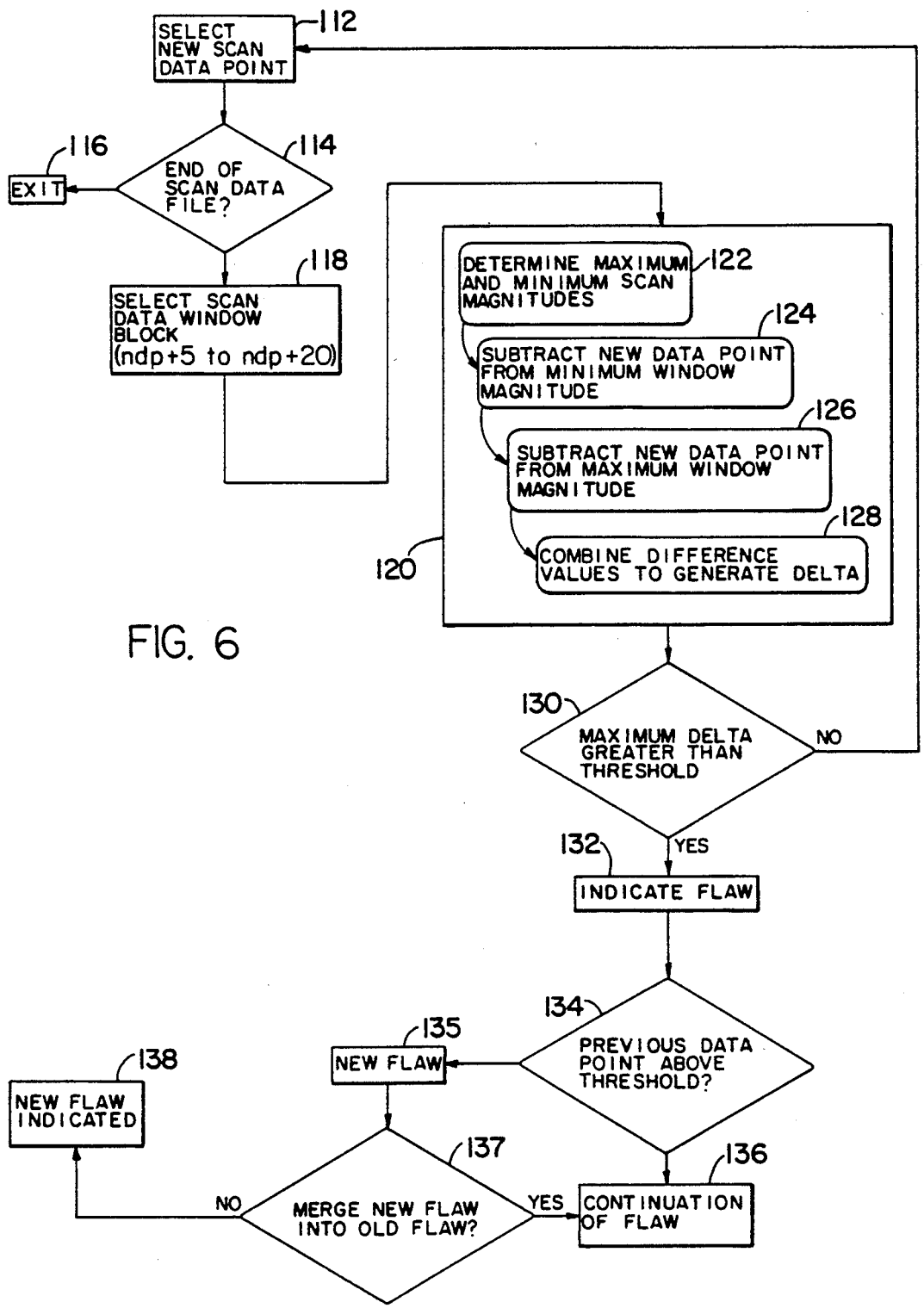
FIG. 6 is a diagrammatic illustration of a second algorithm executed by the system of FIG. 1

Once a flaw has been indicated in the preferred embodiment it is advantageous to determine whether a new flaw has been detected or whether the above threshold signal is indicative of a continuation of an existing flaw. Referring now to FIG. 6 there is shown in simplified diagrammatic form an algorithm 110 provided according to the present invention which provides for such analysis. Initially at block 112 a new scan data point is selected. This scan data point has been previously determined to possess a peak to peak value greater than the threshold value. The algorithm checks to see if an end of file is present (block 114). If an end of file is detected the program exits (block 116).

If no end of file is detected the algorithm proceeds and at block 118 selects a scan data window comprising a block of scan data signals, preferably the new scan data signal (NDP) plus 5 to the new scan data signal plus 20 for 15 total scan data signals. The delay and length of the window from the new data point is associated with the physical parameters of the probe size and data sampling interval. At block 120 the maximum scan magnitude delta is determined. This value corresponds to the maximum peak to peak excursion of the signal over the scan data window. It is ascertained by first determining the maximum and minimum scan magnitudes over the scan data window (block 122). The new data point is then subtracted from the minimum window magnitude (block 124) and the new data point is subtracted from the maximum window magnitude (block 126). The difference values therebetween are combined to generate a delta value for the maximum scan magnitude (block 128). The maximum scan magnitude delta value is compared at block 130 with the flaw threshold value. Should that value be greater than the threshold, a flaw is indicated (block 132). A comparison is made at block 134 with the previous data signal to see if that data signal magnitude exceeded the threshold. If the previous data signal is above the threshold the algorithm indicates a continuation of the flaw (block 136), otherwise a new flaw has been found (block 137). A new flaw is merged with an old flaw if its center location is within a coincidence distance (related to probe size) of the center of the old flaw. For TAM 189532 probe this distance is 0.125 inches. This defines a coincidence window, (block 137). If the new flaw is not within the coincidence window a new flaw indication is generated (block 138).

The present invention can also be used to examine for flaws in out of round workpiece ports or holes. In that application a rotating probe is substituted for probe 14 with appropriate changes to the probe translation mechanism. The probe diameter is selected to be less than 0.010 inch less than the diameter of the hole. Known eddy current inspection techniques for hole wall surface flaw analysis assume constant distance from the probe to the side of the hole. This assumption is clearly erroneous, since hole walls in workpieces can easily have variations in diameter of such a magnitude that eddy current analysis by known techniques would result in undetected flaws. However, with the present invention the probe hole wall separation can be readily determined, allowing for compensation for out of roundness and more accurate flaw detection.

Similarly, although the invention has been shown and described with respect to a preferred embodiment thereof, it should be understood by those skilled in the art that various other changes, omissions and additions thereto may be made therein without departing from the spirit and scope of the present invention.

I claim:

1. A system for use in determining the presence of flaws in a workpiece having a surface, comprising:
   a probe means having at least one inductive coil in a tip, said probe located in noncontacting proximity to the workpiece surface;
   a probe movement means for controllably advancing said probe across said surface;
   an eddy current signal generator means electrically coupled with said probe means and a second inductive coil together comprising a null balanced circuit; said circuit having an electrical signal flowing therethrough; and
   a computer means for receiving data signals from said eddy current signal generator means and for providing signals to said eddy current signal generator means and said probe movement means that control the operation thereof, said computer means including:
   a means for generating control signals to advance said probe across a flaw in the surface of a standard magnitude;
   a means for calibrating said system by generating a table of signals corresponding to the amplitude of said circuit signal as a function of as said probe is advanced across said standard flaw;
   a means for generating baseline vector signals corresponding to the vector magnitudes of said circuit signals as said probe is scanned across said workpiece surface as a function of probe-workpiece surface separation distance;
   a means for scanning said workpiece surface with said probe to generate scan data signals;
   a means for determining from said scan data signals values of probe-workpiece surface separation distance per unit length of said workpiece surface scan by computing vector magnitudes therefor;
   a means for comparing each of said scan data signals with said standard flaw signals at the equivalent probe-workpiece surface separation distance; and
   a means for providing a signal indicative of a flaw should the magnitude of a scan data signal exceed a preselected flaw threshold value.

2. A method for determining the presence of flaws in a workpiece having a surface, comprising the steps of:
   providing a measurement system including a noncontact probe in proximity to the surface having at least one inductive coil in a tip electrically configured with an eddy current measurement means and a second inductive coil together comprising a null balanced circuit with an electrical signal flowing there through, further providing a means for advancing said probe across said surface;
   generating control signals to advance said probe across a flaw of a standard magnitude in the surface;
   calibrating said system by generating a table of signals corresponding to the amplitude of said null balanced circuit signal as a function of probe-workpiece surface separation distance as said probe is advanced across said standard flaw;
   generating baseline vector signals corresponding to the vector magnitudes of said circuit signals as said probe is scanned across said workpiece surface as a function of probe-workpiece surface separation distance;
   scanning said workpiece surface with said probe to generate scan data signals;
   determining from said scan data signals values of probe-workpiece surface separation distance per unit length of said workpiece surface scan by computing vector magnitudes therefor;
   comparing each of said scan data signals with said standard flaw signals at the equivalent probe-workpiece surface separation distance; and
   providing a signal indicative of a flaw should the magnitude of a scan data signal exceed a preselected flaw threshold value.

3. The system of claim 1 further comprising a means for processing said scan data signals to smooth signal magnitude fluctuations therein.

4. The system of claim 3 wherein said signal processing means further comprises a means for computing a 20 data point running average of said scan data signals.

5. The method of claim 2 further comprising the steps of processing said scan data signals to smooth signal magnitude fluctuations therein.

6. The method of claim 5 wherein said signal processing step further comprises the step of computing a 20 data point running average of said scan data signals.

7. The system of claim 1 wherein said computer means for each scan data signal further comprises:
   a means for selecting a scan data window comprised of a block of scan data signals;
   a means for determining maximum and minimum magnitudes of said scan data signals in said scan data window;
   a means for substracting a current scan data signal magnitude from said maximum scan data window signal magnitude to generate a maximum signal difference value;
   a means for substracting said current scan data signal magnitude from said minimum scan data window signal magnitude to generate a minimum signal difference value;
   a means for combining said minimum and maximum difference values to generate a delta signal value;
   a means for comparing said delta signal value with said threshold value;
   a means for generating a signal indicative of a flaw if said delta signal value is greater than or equal to said threshold value;
   a means for determining, if a flaw signal has been generated, whether a flaw signal had been generated for the previous scan data point;
   a means for generating a signal indicative of a continuation of surface flaw should a flaw signal have been generated for the previous scan data point; and
   a means for generating a signal indicative of a new flaw should a flaw signal have not been generated for the previous scan data point.

8. The method of claim 2 further comprises, for each scan data signal, the steps of:
   selecting a scan data window comprised of a block of scan data signals;
   determining maximum and minimum magnitudes of said scan data signals in said scan data window;
   subtracting a current scan data signal magnitude from said maximum scan data window signal magnitude to generate a maximum signal difference value;
   subtracting said current scan data signal magnitude from said minimum scan data window signal magnitude to generate a minimum signal difference value;

combining said minimum and maximum difference values to generate a delta signal value;

comparing said delta signal value with said threshold value;

generating a signal indicative of a flaw if said delta signal value is greater than or equal to said threshold value;

determining, if a flaw signal has been generated, whether a flaw signal had been generated for the previous scan data point;

generating a signal indicative of a continuation of flaw should a surface flaw signal have been generated for the previous scan data point; and generating a signal indicative of a new flaw should a flaw signal have not been generated for the previous scan data point.

9. The system of claim 1 wherein the workpiece surface is curved and said probe movement means further comprises a means for advancing said probe so as to follow said surface curvature.

10. The system of claim 7 wherein said computer means further comprises means for comparing, after determining the presence of a new flaw, the new data signal with data signals in said scan window and generating signals indicative of a continuation of said flaw if a flaw signal has been generated for one of said signals in said scan window.

* * * * *

UNITED STATES PATENT AND TRADEMARK OFFICE
CERTIFICATE OF CORRECTION

PATENT NO. : 5,130,651

DATED : July 14, 1992

INVENTOR(S) : Willard C. Morrey, Jr.

It is certified that error appears in the above-identified patent and that said Letters Patent is hereby corrected as shown below:

In column 10 please make the following changes:

Line 31, the word "substracting" should be --subtracting--.

Line 35, the word "substracting" should be --subtracting--.

Signed and Sealed this

Fifth Day of October, 1993

Attest:

BRUCE LEHMAN

Attesting Officer

Commissioner of Patents and Trademarks